United States Patent [19]

Carrico

[11] Patent Number: 4,743,535
[45] Date of Patent: May 10, 1988

[54] HYBRIDIZATION ASSAY EMPLOYING LABELED PROBE AND ANTI-HYBRID

[75] Inventor: Robert J. Carrico, Elkhart, Ind.

[73] Assignee: Miles Inc., Elkhart, Ind.

[21] Appl. No.: 668,255

[22] Filed: Nov. 7, 1984

[51] Int. Cl.[4] .................. C12Q 1/68; G01N 33/537; G01N 33/542
[52] U.S. Cl. .......................... 435/6; 435/7; 435/810; 436/536; 436/537; 436/805; 436/808; 935/78
[58] Field of Search .......... 435/6, 7, 91, 810; 436/501, 512, 513, 518, 536, 800, 805, 808, 63, 537; 935/2, 15, 77, 78, 81

[56] References Cited

U.S. PATENT DOCUMENTS

| | | | |
|---|---|---|---|
| 3,935,074 | 1/1976 | Rubenstein et al. | 435/22 X |
| 4,238,565 | 12/1980 | Hornby et al. | 435/7 |
| 4,358,535 | 11/1982 | Falkow et al. | 435/6 X |
| 4,463,090 | 7/1984 | Harris | 435/810 X |
| 4,493,899 | 1/1985 | Smith et al. | 435/6 X |
| 4,547,569 | 10/1985 | Letsinger et al. | 536/23 X |
| 4,563,417 | 1/1986 | Albarella et al. | 435/7 X |
| 4,581,333 | 4/1986 | Konrilsky et al. | 435/6 |
| 4,623,627 | 11/1986 | Huang et al. | 436/548 |

FOREIGN PATENT DOCUMENTS

| | | |
|---|---|---|
| 63879 | 11/1982 | European Pat. Off. |
| 0070685 | 1/1983 | European Pat. Off. |
| 87564 | 9/1983 | European Pat. Off. |
| 95089 | 11/1983 | European Pat. Off. |
| 93613 | 11/1983 | European Pat. Off. |
| 0135159 | 3/1985 | European Pat. Off. |
| 0144914 | 6/1985 | European Pat. Off. |

OTHER PUBLICATIONS

Lewin (1983) Science 221:1167.
Raap et al. (1984) Histochemistry 81:517–520.
Stuart et al. (1981) Proc. Nat'l. Acad. Sci. 78(6):3751–3754.
Nakazato et al. (1980) Biochemistry 19:2835–2840.
Poirier et al. (1982) Proc. Nat'l. Acad. Sci. 79:6443–6447.
Stumph et al, Biochemistry, vol. 17, No. 26, pp. 5791–5798 (1978).
Schwartz et al, Chemical Abstracts, vol. 70, No. 25, p. 168, No. 1133rrd (1969).
Reddy and Sofer, Biochem. Biophys. Res. Commun. 103:959 (1981).
Rudkin and Stollar, Nature 165:472 (1977).
Van Prooijen-Knedt et al., Exp. Cell Res. 141:397 (1982).

Primary Examiner—Esther M. Kepplinger
Attorney, Agent, or Firm—Andrew L. Klawitter

[57] ABSTRACT

A nucleic acid hybridization assay involving a labeled probe and formation of a hybrid having epitopes for an antibody reagent. The label provides a detectable response which is measurably different when the labeled probe is comprised in a hybrid that is bound by the antibody reagent compared to when not comprised in such a hybrid. Particularly useful antibody reagents are antibodies such as anti-DNA.RNA, anti-RNA.RNA and antibodies to intercalated duplexes which do not bind substantially to single stranded nucleic acids. Modulation of the label response can be accomplished in a variety of ways such as by steric inactivation or hindrance or by labeling the antibody reagent with a second label which interacts with the first label. The assay is particularly advantageous because no separation of hybridized and unhybridized probe is required.

46 Claims, 3 Drawing Sheets

COMBINE:

1. SINGLE STRANDED SAMPLE NUCLEIC ACIDS (S)

2. FLUORESCER-LABELED PROBE (P)

3. ANTI-HYBRID AND ANTI-FLUORESCER

+

COMBINE:

1. SINGLE STRANDED SAMPLE NUCLEIC ACIDS

2. FLUORESCER - LABELED PROBE

3. QUENCHER - LABELED ANTIBODY

+

HYBRIDIZATION ASSAY EMPLOYING LABELED PROBE AND ANTI-HYBRID

FIELD OF THE INVENTION

This invention relates to nucleic acid hybridization assay methods and reagent systems for detecting specific polynucleotide sequences. The principle of nucleic acid hybridization assays was developed by workers in the recombinant DNA field as a means for determining and isolating particular polynucleotide base sequences of interest. It was found that single stranded nucleic acids, e.g., DNA and RNA, such as obtained by denaturing their double stranded forms, will hybridize or recombine under appropriate conditions with complementary single stranded nucleic acids. By labeling such complementary probe nucleic acids with some readily detectable chemical group, it was then made possible to detect the presence of any polynucleotide sequence of interest in a test medium containing sample nucleic acids in single stranded form.

In addition to the recombinant DNA field, the analytical hybridization technique can be applied to the detection of polynucleotides of importance in the fields of human and veterinary medicine, agriculture, and food science, among others. In particular, the technique can be used to detect and identify etiological agents such as bacteria and viruses, to screen bacteria for antibiotic resistance, to aid in the diagnosis of genetic disorders such as sickle cell anemia and thalassemia, and to detect cancerous cells. A general review of the technique and its present and future significance is provided in Biotechnology (August 1983), pp. 471-478.

INFORMATION DISCLOSURE

The following information is provided for the purpose of making known information believed by the applicant to be of possible relevance to the present invention. No admission is necessarily intended, nor should be construed, that any of the following information constitutes prior art against the present invention.

The state-of-the-art nucleic acid hybridization assay techniques generally involve a separation of hybridized and unhybridized labeled probe. This required separation step is usually facilitated by immobilizing either the sample nucleic acids or the nucleic acid probe on a solid support. Commonly, hybridization between particular base sequences or genes of interest in the sample nucleic acids and a labeled form of the probe nucleic acid is detected by separating the solid support from the remaining reaction mixture which contains unhybridized probe, followed by detection of the label on the solid support.

There are continuing efforts to simplify the analytical procedure for performing nucleic acid hybridization assays. A primary goal of these efforts is to reduce the complexity of the procedure to the point that it can be conveniently and routinely performed in clinical laboratories. The necessity of a separation step seriously impedes the progress of these efforts. The separation step requires considerable expertise in order to be accomplished in an analytically reproducible manner and is a physical manipulation not readily automated or suited to high volume testing.

Moreover, in conventional methods involving the immobilization of sample nucleic acids, two significant difficulties are encountered. Firstly, the procedures required to accomplish immobilization are generally time consuming and add a further step which is undesirable for routine use of the technique in a clinical laboratory. Secondly, proteins and other materials in the heterogeneous sample, particularly in the case of clinical samples, can interfere with the immobilization process.

As alternatives to immobilizing sample nucleic acids and adding labeled probe, one can use an immobilized probe and label the sample nucleic acids in situ, or one can use a dual hybridization technique requiring two probes, one of which is immobilized and the other labeled. The former alternative, however, is even less desirable since the in situ labeling of the sample nucleic acids requires a high degree of technical skill which is not routinely found in clinical technicians and there are no simple, reliable methods for monitoring the labeling yield, which can be a significant problem if the labeling media contain variable amounts of inhibitors of the labeling reaction. The dual hybridization technique has the disadvantages of requiring an additional reagent and incubation step and the kinetics of the hybridization reaction can be slow and inefficient. The accuracy of the assay can also be variable if the complementarity of the two probes with the sample sequence is variable.

Some of the problems discussed above are solved by employing an immobilized RNA probe and detecting resulting immobilized DNA.RNA or RNA.RNA hybrids with a labeled specific anti-hybrid antibody [see commonly assigned U.S. Pat. application Ser. No. 616,132, filed June 1, 984]. This technique still requires a separation step and thus has the disadvantages common to all hybridization techniques that require a separation step as discussed above.

European patent application No. 70,685 proposes a hybridization assay technique that dispenses with the need to physically separate hybridized from unhybridized probe. It is proposed to employ a pair of probes which hybridize to contiguous regions on a polynucleotide sequence of interest and to label one probe with a chemiluminescent catalyst such as the enzyme peroxidase and the other with an absorber molecule for the chemiluminescent emission. The catalyst and absorber labels must be situated near the contiguous terminal ends of the respective probes such that upon hybridization there is observed quenching of the chemiluminescent emission by energy transfer to the absorber molecule. In order to perform such an assay, one must be able to controllably synthesize two critical probe reagents such that the respective labels are brought into a quenching orientation upon hybridization to the sample nucleic acid and without affecting the affinity of the respectively labeled probe segments to actually undergo hybridization.

SUMMARY OF THE INVENTION

A nucleic acid hybridization assay has now been devised based on modulation of the detectable response of hybridized labeled probe by binding of an antibody reagent to the hybrid formed between the labeled probe and the particular polynucleotide sequence to be detected. Thus, the label in the antibody-bound hybrid expresses a detectably different response than the response expressed by the label in unhybridized labeled probe. In this way there is no need to separate hybridized and unhybridized probe, greatly facilitating the performance and automation of the assay. In addition, the assay signal is nonradioisotopic in nature thereby meeting another criterion of assay convenience, the use of detection systems not involving radioactivity.

According to the present invention, specific nucleotide sequences are detected in a test sample by forming a hybrid between any of the particular sequence to be detected and a labeled nucleic acid probe comprising a label and at least one single stranded base sequence that is substantially complementary to the sequence to be detected. The hybrid is characterized by having epitopes for an antibody reagent (anti-hybrid) which does not bind substantially to single stranded nucleic acids. Anti-hybrid is then added and will not substantially bind to the labeled probe unless it is present hybridized to the sequence to be detected. The label in the labeled probe provides a detectable response which is measurably different, i.e., increased or decreased, when the labeled probe is comprised in a hybrid that is bound by anti-hybrid compared to when not comprised in such a hybrid. Measurement of the resulting detectable response will be a function of the presence of the sequence to be detected in the sample.

A preferred mechanism of modulation of the label by anti-hybrid binding is understood to involve steric hindrance. In such situations the label interacts chemically with a reagent member of a label detecting system, such as by reaction or binding, and the presence of anti-hybrid bound to the hybrid results in steric hindrance of access of such detection system member to the label. Preferred labels that can be applied to such systems involve enzyme reactions, that is, the label and the reagent member with which the label interacts are selected from enzyme substrates, enzyme cofactors, enzyme inhibitors, and enzymes. Detectable responses that are colorimetric, fluorometric, or luminometric are obtainable.

Another preferred mechanism of modulation of the label by anti-hybrid is based on the use of proximal interacting label pairs. The probe is labeled with one of a first label and a second label and the antibody reagent is labeled with the other, or comprises in its native form a chemical group which serves as the other label, where interaction between the two labels provides a detectable response which is measurably different, either in a positive or a negative sense, when the labeled antibody reagent is bound to a hybrid comprising the labeled probe compared to when not so bound. When associated in the same hybrid, the two labels are brought to within a proximate interaction distance of one another, thereby substantially increasing signal affecting interactions between the two labels compared to the relatively less frequent interactions occurring in the bulk solution between the free diffusible labeled reagents. A preferred interaction between the two labels is a sequential interaction wherein the first label participates in a first chemical reaction to produce a diffusible product that is a participant in a second chemical reaction with the second label to produce a detectable product. It is especially preferred that the first and/or second labels be catalysts for the first and second chemical reactions, respectively. For example, the antibody reagent can be labeled with an enzyme and the probe with a catalyst which acts on a diffusible product of the enzyme reaction to give a product which is detectable such as by an optical signal in the presence of suitable indicator dye compositions. Another preferred labeling pair is that involving energy transfer interaction such as between a fluorescer or luminescer and a quencher for the photoemission of the first label.

The present invention is characterized by a number of significant advantages. In addition to the principal advantage of elimination of the separation step, there is no requirement to immobilize either sample or probe nucleic acids which gives rise to nonspecific binding and reproducibility problems in commonly used hybridization techniques. Further, the hybridization kinetics are substantially faster in solution compared to systems with one strand of the hybridizable pair immobilized. An additional advantage is that the assay can be performed without wash steps. The assay reagents can be sequentially added to the hybridization medium without the need to wash insoluble support materials.

Another significant feature of the present invention is that the detection systems involved can be particularly efficient since the double stranded duplexes can contain many labels and binding sites for the anti-hybrid reagent. This results in large amounts of the label and anti-hybrid becoming assembled into their interactive configuration per unit of hybridized probe. In considering antibodies to RNA.DNA or RNA.RNA hybrids, one labeled antibody can bind for approximately each 10 base pairs of the hybrid. If the probe is for example 500 bases long, 40–50 antibodies could bind. The presence of multiple binding sites on hybrids can be used advantageously when low levels of hybrid must be detected.

DESCRIPTION OF THE PREFERRED EMBODIMENTS

Figure 1:
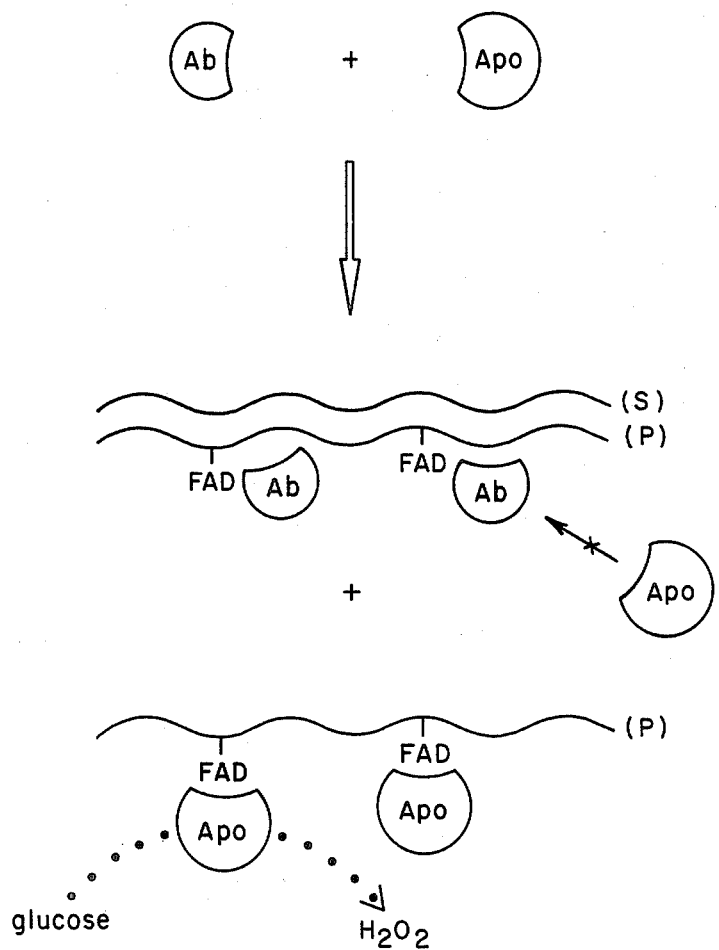
FIGS. 1–3 are schematic illustrations of preferred methods for performing the present invention. These methods are described in detail below.

The use of nucleic acid hybridization as an analytical tool is based fundamentally on the double-stranded, duplex structure of DNA. The hydrogen bonds between the purine and pyrimidine bases of the respective strands in double-stranded DNA can be reversibly broken. The two complementary single strands of DNA resulting from this "melting" or "denaturation" of DNA will associate (sometimes referred to as reannealing or hybridization) to reform the duplexed structure. As is now well known in the art, contact of a first single stranded nucleic acid, either DNA or RNA, which comprises a base sequence sufficiently complementary to (i.e., "homologous with") a second single stranded nucleic acid under appropriate conditions, will result in the formation of DNA.DNA, RNA.DNA, or RNA.RNA hybrids, as the case may be.

The Probe

The probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear, or they can be self-complementary and form hairpin loops. In addition, the homologous region of the probe can be flanked at the 3'-and 5'-termini by nonhomologous sequences, such as those comprising the DNA or RNA of a vector into which the homologous sequence had been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. It will generally be preferred to employ probes which are substantially in single stranded form. The preparation of a suitable probe for a particular assay is a matter of routine skill in the art.

The Label

The label can be selected from a wide variety of materials. Essentially any material can be used as the label which when comprised in the labeled probe provides a detectable response that is modulatable by binding of anti-hybrid and which is sufficiently stable under the conditions of hybridization to provide a measurable response. Modulation or modification of the label response can be the result of a variety of different effects which occur upon binding of anti-hybrid to the hybrid.

A particularly preferred mechanism of modulation of the label response is understood to involve steric hindrance. Normally, the label is selected to provide the detectable assay response upon interaction such as by chemical reaction or binding with a member of a reagent detection system comprising one or more substances which participate with the label to provide the measured signal. Whether due to steric hindrance or some other phenomenon, the binding of anti-hybrid will interupt or inactivate the label from such signal generating participation. Such effect on the signal generation will reflect the presence of hyridized labeled probe.

Preferably, when involved in a steric hindrance-based system, the label will be small, e.g., of molecular weight less than 10,000, more usually less than 4,000, and preferably less than 2,000 daltons, and the interactive reagent in the preferred detection system will normally be significantly larger, e.g., more than 3 times larger, more usually 10 times larger, and preferably 20 to 100 times or more larger then the label. Accordingly, in the most preferable systems with labels having masses of the order to 100 to 2,000 daltons, at least one member of the detection system with which the label must interact to provide the detectable signal will be of the order of 10,000 to 200,000 daltons or greater. Such size relationship between the label and the detection system member increases the probability of a significant steric effect upon binding of anti-hybrid with the labeled hybrid. Preferred labels therefore are participants in an enzyme-catalyzed reaction, such as enzyme substrates, coenzymes, enzyme prosthetic groups, and enzyme inhibitors, since a wide variety of enzymic reactions are available from which to chose assay components. Many small substrates, coenzymes, and inhibitors are known for enzymes of sufficiently large molecular weignt to have the preferred size relationship between label and its interacting detection system member. This applies likewise for prosthetic groups and their corresponding apoenzymes. Nonproteinaceous, and particularly stable organic or inorganic, compounds will be preferable as labels due to the denaturing conditions under which hybridization is performed.

Some particularly preferred labels and approaches for preparing the labeled probe are discussed below.

Enzyme Substrate Labels

In this system, the label is selected so that the labeled probe is a substrate for an enzyme and the ability of the enzyme to act on the substrate-labeled probe is affected, either in a positive or negative sense, but usually in an inhibitory fashion, by binding of the labeled probe with anti-hybrid. Action of the enzyme on the substrate-labeled probe produces a product that is distinguishable in some feature, usually a chemical or physical feature such as chemical reactivity in an indicator reaction or such as a photometric character, e.g., fluorescence or light absorption (color). Labels of this type are described in general terms in commonly assigned, copending application Serial No. 894,836, filed April 10, 1978 (corresponding to U.K. Pat. Spec. 1,552,607); and in Anal. Chem. 48:1933(1976), Anal. Biochem. 77:55(1977) and Clin. Chem. 23:1402(1977). In such enzyme substrate-labeled techniques, the labeled probe will have the property that it can be acted upon by an enzyme, by cleavage or modification, to produce a product having a detectable property which distinguishes it from the conjugate. For example, the conjugate can be nonfluorescent under assay conditions but upon reaction with enzyme a fluorescent product is produced.

A very useful class of substrate labels includes those which undergo simple hydrolysis reactions to yield fluorescent products. Such products can be detected at low concentrations. Examples of these types of substrates are phosphate esters, phosphodiesters, and glycosides of fluorescent dyes. Glycosides are especially preferred since their rates of nonenzymatic hydrolysis are low, and β-galactosides are particularly advantageous because β-galactosidase enzymes are readily available and very stable.

A particular class of useful fluorogenic substrate-labeled probe conjugates are of the formula:

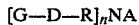

wherein G is a cleavable group such as phosphate, carboxylate., sulfate, or glycone, D is a fluorogenic dye moiety which upon removal of G yields a fluorescent product, e.g., D can be umbelliferone, fluorescein, rhodamine, and their derivatives, R is a linking group, NA is the nucleic acid probe and n is the average number of labels per molecule of probe, e.g., between 1 and 50. Enzymatic cleavage (e.g., by phosphatase, carboxylase, sulfatase, glycosidase, etc.) of the labeled conjugate is affected by binding of anti-hybrid to the labeled hybrid. See U.S. Pat. No. 4,279,992. A particularly preferred substrate-labeled assay scheme employs a labeled conjugate of the type:

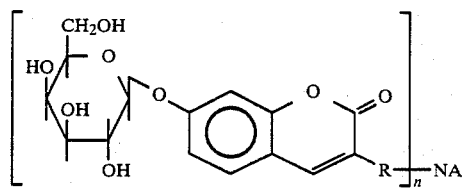

wherein R, NA, and n are as defined above, whereby the ability of the enzyme β-galactosidase to cleave the conjugate yielding a product distinguishable by its fluorescence is inhibited by binding of the labeled hybrid with anti-hybrid.

Other useful substrate-labeled conjugates are those of the formula:

[D—X]$_n$NA wherein X is an enzyme cleavable linking group, e.g., phosphate, carboxylate, and the like, NA and n are as defined above, and D is a fluorogenic dye moiety as above which upon cleavage of X releases a fluorescent indicator. A labeled conjugate of this type has the formula:

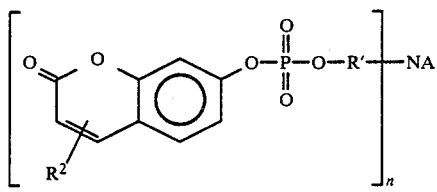

wherein R$^1$ is a bond or chain linking the labeled component NA to the cleavable phosphate group and R$^2$ is hydrogen or a substituent group such as lower alkyl, e.g., methyl and ethyl, N-alkylamido or N-(hydroxy-substituted lower alkyl)amido, e.g., —COHN—(CH$_2$-)$_m$—OH wherein m=2-6 (see U.S. Pat. No. 4,273,715). The umbelliferone residue may bear other or additional substituents [see Anal. Chem. 40:803(1968)]. Cleavage by phosphodiesterase is affected by binding of anti-hybrid to the labeled hybrid. In the process, some of the phosphodiester linkages in the hybrid can be cleaved as well but will not affect the assay since hybridization will have been completed and the modulation of cleavage of the substrate label will be essentially the same for labels present in intact hybrids compared to digested fragments thereof.

Another preferred fluorescent dye is 6-carboxyfluorescein which has fluorescence excitation and emission maxima at 490 and 520 nm, respectively, and can be synthesized by the method of Ullman et al, (1976), J. Biol. Chem. 251:4172. It can be converted to the di-β-galactoside by the method of Rotman et al, Proc. Nat'l Acad. Sci. 50, 1(1963). This product can be converted to the N-hydroxysuccinimide ester by the method described by Khanna and Ullman, Anal. Biochem. 108:156(1980) for preparation of the coresponding ester of 4',5'-dimethoxy-5-carboxymethylfluorescein.

Enzyme Cofactor Labels

The labeled probe in this system is composed, in its label portion, of a coenzyme-active functionality, and the ability of such coenzyme label to participate in an enzymatic reaction is affected by binding of the labeled hybrid by anti-hybrid. The rate of the resulting enzymatic reaction is measurable by conventional detectant systems to yield an ultimately detectable signal. Labels of this type are described in commonly assigned, copending application Ser. No. 894,836, filed April 10, 1978 (corresponding to U.K. Pat. Spec. No. 1,552,706); and in Anal. Biochem 72:271(1976), Anal. Biochem 72:283(1976) and Anal. Biochem. 76:95(1976).

A useful coenzyme for labeling is nicotamamide adenine dinucleotide (NAD). NAD can be coupled to the probe through a bridge at the 6-nitrogen or the 8-carbon of the adenine moiety. A method for introduction of an aminoethyl bridge at the 6-nitrogen position is described by Carrico et al, Anal. Biochem 72:271(1976). Lee and Kaplan, Arch. Biochem. Biophys. 168:665(1976) have described a synthesis for introduction of a diaminohexane bridge at the 8-carbon. The NAD labels can be detected in a variety of ways such as by enzymic cycling with malic dehydrogenase and alcohol dehydrogenase.

Another useful coenzyme is adenosine triphosphate (ATP). Trayer et al, Biochem. J. 139:609(1974) have described the synthesis of ATP with a hexylamine bridge on the 6-nitrogen of the adenine group. This can be detected by enzymic cycling with hexokinase and pyruvate kinase. ATP can also be coupled to the probe through the ribose ring. The ribose is oxidized with sodium periodate and then condensed with a dihydrazide (Wilchek and Lamed, Meth. in Enzymol., 34B:475(1974)]. The resulting hydrazone is reduced with sodium borohydride. This label can be detected sensitively with firefly luciferase in a bioluminescent readout.

A particularly useful class of cofactor labels are prosthetic groups. In such systems, the ability of a catalytically inactive apoenzyme to combine with the prosthetic group label to form an active enzyme (holoenzyme) is affected by binding of the labeled hybrid by anti-hybrid. Resulting holoenzyme activity is measurable by conventional detectant systems to yield an ultimate detectable signal. Labels of this type are described in commonly owned U.S. Pat. No. 4,238,565. A particularly preferred prosthetic group-labeled assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide. Fluorometric detection of hydrogen peroxide is also possible using an appropriate fluorogenic substrate. FAD can be coupled to the probe through a bridge group at the 6-nitrogen of the adenine moiety. Morris et al, Anal. Chem. 53:658(1981) describe a procedure for synthesis of FAD with a hexylamine bridge at the 6-nitrogen and Zappelli et al, Eur. J. Biochem. 89:491(1978) describe a method for introduction of a 2-hydroxy-3-carboxypropyl group at the same position.

Enzyme Modulator Labels

The labeled probe in this system is composed, in its label portion, of an enzyme modulating functionality such as an enzyme inhibitor or stimulator, and the ability of such modulator label to modulate the activity of an enzyme is affected by binding of the labeled hybrid by anti-hybrid. The rate of the resulting enzymatic reaction is measurable by conventional detectant systems to yield an ultimately detectable signal. Labels of this type are described in U.S. Pat. Nos. 4,134,792 and 4,273,866. Particularly preferred is the use of methotrexate as the label with dihydrofolate reductase as the modulated enzyme. Where the label is an enzyme inhibitor, it may interact with the enzyme covalently or noncovalently, and may be a small molecule, e.g., methotrexate, or a large molecule, e.g., antibody to enzyme (see U.S. Pat. No. 4,273,866 and commonly assigned, copending application Serial No. 285,605, filed July 21, 1981).

Catalyst Labels

In this system, the label is a catalyst and the activity of the catalyst label is affected by binding of the labeled hybrid by anti-hybrid. Resulting catalytic activity is measurable by conventional detectant systems to yield an ultimately detectable signal, e.g., absorption or fluorescence. Labels of this type are described in U.S. Pat. No. 4,160,645.

Epitope Labels

In this system, the label comprises an epitope, i.e., an antibody binding site, for a second antibody, i.e., anti-label, or fragment thereof. The ability of anti-label to bind to label in the labeled hybrid is affected by binding of anti-hybrid. Several monitoring or detection schemes are possible. In one instance, the epitope label also is a fluorescer whose light emission is altered, e.g., reduced upon binding with anti-fluorescer. Anti-hybrid binding to labeled hybrid restricts accessibility of the fluorescer label to the quenching anti-fluorescer (see U.S. Pat. No. 3,998,943). In another approach, an additional detector molecule is used comprising the epitope label coupled to an enzyme. Binding of anti-label to this epitope-enzyme conjugate results in inhibition of enzyme activity. The more anti-label is excluded from binding label on the epitope-labeled hybrid by anti-hybrid binding, the more anti-label is available to bind to and inhibit enzyme activity of the epitope-enzyme reagent (see U.S. Pat. No. 3,935,074).

Labeling Pairs

According to another preferred embodiment of the present invention, a pair of labels are used such that hybridization dependent upon the presence of the polynucleotide sequence of interest and binding to a labeled antibody reagent to the labeled hybrid results in the bringing together of the two labels within a certain distance such that the signal produced by their interaction is measurably different from that produced by their encounters during simple diffusion in the bulk assay medium. Various interaction phenomena can be applied to this embodiment. The interaction can be chemical, physical, or electrical, or combinations of these forces. The environment of the labels which is created upon hybridization and binding of the labeled antibody reagent to the formed labeled hybrid, herein referred to as the bound hybrid environment, must be distinctively different in at least one critical aspect from the bulk medium. Since hybridization determines the proportion of labels which result in the localized hybrid environment compared to the bulk phase, the resulting signal response is dependent upon the presence of the sequence to be determined in the assay medium.

A preferred interaction between the two labels involves two chemical reactions wherein one label participates in the first reaction to produce a diffusible mediator product which participates in the second reaction with the second label to yield a detectable product. The microenvironment of the bound hybrid will thus contain a higher localized concentration of the mediator product, so as to increase the rate of the signal producing second label reaction, than the bulk solution. The two labels, respectively, can participate in the reactions as reactants or, as is particularly preferred, catalysts. Any involved catalysis can be either enzymatic or nonenzymatic.

A variety of enzymes and catalysts can be applied to this embodiment and their selection will be a matter of choice to one working in the field. Useful enzymes for labeling the antibody reagent include the oxidoreductases, particularly those involving nucleotides such as nicotinamide adenine, dinucleotide (NAD) or its reduced form (NADH), or adenosine triphosphate (ATP) as cofactors or those producing hydrogen peroxide or other small diffusible products. A few examples are alcohol dehydrogenase, glycerol dehydrogenase, lactate dehydrogenase, malate dehydrogenase, glucose-6-phosphate dehydrogenase, glucose oxidase, and uricase. Other classes of enzymes such as hydrolases, transferases, lyases, and isomerases can also be employed. A detailed listing and description of useful enzymes is provided in U.S. Pat. Nos. 4,233,402 and 4,275,149 incorporated herein by reference. Other useful systems involve one enzyme as the first label which catalyses a reaction producing a prosthetic group for an apoenzyme or proenzyme. Nonenzymatic catalysts can also serve as labels as previously mentioned. By way of example, reference is made to U.S. Pat. No. 4,160,645.

Another preferred interaction between label pairs is that of energy transfer. The first label will be a photoemitting substance such as a fluorescer or luminescer, the former producing an emission upon irradiation and the second producing an emission upon chemical reaction. The photoemission is absorbable by the second label to either quench the emission or to provide a second emission such as where the absorbing label is a fluorescer itself. Pairings of compounds useful for this effect are described in detail in U.S. Pat. Nos. 4,275,149 and 4,318,981. Some preferred fluorescer/quencher pairs are naphthalene/anthracene, α-naphthylamine/dansyl, tryptophan/dansyl, dansyl/fluorescein, fluorescein/rodamine, tryptophan/fluorescein, N-[p-(2-benzoxazolyl)phenyl]maleimide (BPM)/thiochrome, BPM/8-anilino-1-naphthalenesulfonate (ANS), thiochrome/N-(4-dimethylamino-3,5-dinitrophenyl) maleimide (DDPM), and ANS/DDPM. Some preferred luminescer/quencher pairs are luminol with fluorescein, eosin or rhodamine S.

If desired, various modifications of the labeled probe can be employed without departing from the scope of the present invention. In one variation, the labeled probe comprises a solid phase to which the label is linked. The solid phase can be the walls of the reaction container or a dispersed solid such as a polyacrylamide or agarose bead. One could also modify the probe with a bindable ligand such as a hapten or biotin and introduce the label by addition of a labeled anti-hapten antibody or labeled avidin before or after the hybridization reaction. Thus, it can be seen that the label can be linked to the binding substance directly or indirectly through intermediary components.

Labeling the Probe

A variety of methods can be used to label polynucleotide probes. It is preferable to have the label distributed along the length of the polynucleotide rather than clustered at one position. Several means for labeling are outlined below.

5-(3-Amino)allyldeoxyuridine triphosphate (AA-dUTP) can be synthesized by the method of Langer et al, Proc. Nat'l. Acad. Sci. 78:6633(1981) and can be introduced into double stranded DNA probes by nick translation with DNA polymerase. The probe will have pendant amino groups which can be reacted with the labels described above.

The N-hydroxysuccinimide esters of 6-carboxyfluorescein, 4',5'-dimethoxy-6-carboxymethylfluorescein and their β-galactosyl derivatives can be reacted directly with the nick translated probe. The activated dyes would be used in excess to maximize the incorporation of label and then uncoupled dye would be separated from the labeled DNA by a gel filtration method.

The labels with terminal amines on the bridge groups can be coupled to the nick translated DNA by means of bifunctional reagents such as dimethyladipimidate, hexamethylene diisocyanate, and p,p'-difluoro-m,m'-dinitrophenylsulfone. The labels can be reacted with an excess of the bifunctional reagent followed by removal of the unreacted reagent. The activated label can be reacted with the nick translated probe.

Certain planar aromatic compounds intercalate between the base pairs of double stranded nucleic acids to form reversible complexes. Some intercalating agents can be coupled covalently to the polynucleotides by photolysis of the intercalation complexes. Examples of photoactivatable intercalating agents are 8-azidoethidium, 8-azidomethidium, and furocoumarins such as angelicin. These intercalators can be modified with bridge arms containing functional groups. The 8-azidomethidium derivatives can be prepared as described by Hertzberg and Dervan, J. Am. Chem. Soc. 104:313(1982) and Mitchell and Dervan, J. Am. Chem. Soc. 104:4265(1972). The labels can be coupled directly to the modified intercalators. For example, the N-hydroxysuccinimide esters of 6-carboxyfluorescein or 4',5'-dimethoxy-6-carboxyfluorescein can be reacted with the intercalator derivatives to form amide linkages. Then these intercalator-label conjugates can be added to a polynucleotide probe and photolyzed. Alternatively, the modified intercalators can be photolyzed with polynucleotide probe and then coupled to the label compounds. 8-Azidomethidium can be coupled photolytically to single stranded nucleic acids through a nonintercalative mechanism [Balton and Kerns (1978) Nucl. Acids Res. 5:4891]. This means can be used to couple this intercalator derivative to single stranded DNA and RNA.

Anti-Hybrid

A critical aspect of the present invention is the formation of a hybrid between the probe and the polynucleotide sequence of interest which comprises binding sites for the anti-hybrid antibody reagent. A principle of the assay is that hybridization of the labeled probe with the desired sequence results in formation of a hybrid which is bound by the anti-hybrid resulting in a measurable effect on the label response. Any design of the system can be used which results in a binding site for the anti-hybrid reagent which is unique to the hybrid. It will thereby be assured that the desired effect of the binding of anti-hybrid on the probe label will occur only upon formation of the hybrid.

The binding of the anti-hybrid to the hybrid will normally involve a highly specific noncovalent binding such as is characteristic of a variety of biologically derived substances, particularly binding proteins such as immunoglobulins. A variety of binding substances can be used to provide anti-hybrid which has a unique binding affinity for the hybrid with inconsequential binding affinity for single stranded nucleic acids such as unhybridized probe and unhybridized sample nucleic acids.

Particularly preferred binding substances are antibody reagents having anti-hybrid binding activity and can be whole antibodies or fragments thereof, or aggregates or conjugates thereof, of the conventional polyclonal or monoclonal variety. Preferred antibody reagents will be those that are selective for binding (i) DNA·RNA or RNA·RNA hybrids or (ii) intercalation complexes. It is currently known that antibodies can be stimulated which are selective for DNA·RNA or RNA·RNA hybrids over the single stranded nucleic acids, however, it is presently considered infeasible to generate such selectivity in the case of DNA·DNA hybrids. To the extent that selective DNA·DNA antibodies are developed in the future, they will clearly be applicable to the present invention. Antibodies to DNA·RNA hybrids can be used where one of the probe and the sequence to be detected is DNA and the other is RNA and antibodies to RNA·RNA can be used when both the probe and the sequence to be detected are RNA.

Further, it should be understood that in referring to an RNA probe used with an anti-DNA·RNA or anti-RNA·RNA reagents, it is contemplated herein that not all nucleotides comprised in the probe be ribonucleotides, i.e., bearing a 2'-hydroxyl group. The fundamental feature of an RNA probe as used herein is that it be sufficiently non-DNA in character to enable the stimulation of antibodies to DNA·RNA or RNA·RNA hybrids comprising an RNA probe which do not cross-react to an analytically significant degree with the individual single strands forming such hybrids. Therefore, one or more of the 2'-positions on the nucleotides comprised in the probe can be in the deoxy form provided the antibody binding characteristics necessary for performance of the present assay are maintained to a substantial degree. Likewise, in addition or alternatively to such limited 2'-deoxy modification, an RNA probe can comprise nucleotides having other 2'-modifications, or in general any other modification along its ribose phosphate backbone provided there is not substantial interference with the specificity of the antibody to the double stranded hybridization product compared to its individual single strands.

Where such modifications exist in an RNA probe, the immunogen used to raise the antibody reagent would preferably comprise one strand having substantially corresponding modifications and the other strand being substantially unmodified RNA or DNA, depending on whether sample RNA or DNA is intended to be detected. Preferably, the modified strand in the immunogen would be identical to the modified strand in an RNA probe. An example of an immunogen is the hybrid poly(2'-O-methyladenylic acid)·poly(2'-deoxythymidylic acid). Another would be poly(2'-O-ethylinosinic acid)·poly(ribocytidylic acid). The following are further examples of modified nucleotides which could be comprised in an RNA probe: 2'-O-methylribonucleotide, 2-O-ethylribonucleotide, 2'-azidodeoxyribonucleotide, 2'-chlorodeoxyribonucleotide, 2-O-acetylribonucleotide, and the methylphosphonates or phosphorothiolates of ribonucleotides or deoxyribonucleotides. Modified nucleotides can appear in RNA probes as a result of introduction during enzymic synthesis of the probe from a template. For example, adenosine 5'-O-(1-thiotriphosphate) (ATPαS) and dATPαS are substrates for DNA dependent RNA polymerases and DNA polymerases, respectively. Alternatively, the chemical modification can be introduced after the probe has been prepared. For example, an RNA probe can be 2'-O-acetylated with acetic anhydride under mild conditions in an aqueous solvent.

Immunogens for stimulating antibodies specific for RNA·DNA hybrids can comprise homopolymeric or heteropolymeric polynucleotide duplexes. Among the possible, homopolymer duplexes, particularly preferred is poly(rA)·poly(dT) [Kitagawa and Stollar (1982) Mol. Immunol. 19:413]. However, in general, heteropolymer duplexes will be preferably used and can be prepared in a variety of ways including transcription of φX174 virion DNA with RNA polymerase [Nakazato (1980) Biochem. 19:2835]. The selected RNA·DNA duplexes are adsorbed to a methylated protein, or otherwise linked to a conventional immunogenic carrier material, such as bovine serum albumin, and injected into the desired host animal [see also Stollar (1980) Meth. Enzymol 70:70]. Antibodies to RNA·RNA duplexes can be raised against double stranded RNAs from viruses such as reovirus or Fiji disease virus which infects sugar cane, among others. Also, homopolymer duplexes such as poly(rI)·poly(rC) or poly(rA)·poly(rU), among others, can be used for immunization as above. Further information regarding antibodies to RNA·DNA and RNA·RNA hybrids is provided in commonly assigned U.S. patent application Ser. No. 616,132, filed June 1, 1984.

Antibodies to intercalation complexes can be prepared against an immunogen which will usually comprise an ionic complex between a cationic protein or protein derivative (e.g., methylated bovine serum albumin) and the anionic intercalator-nucleic acid complex. Ideally, the intercalator will be covalently coupled to the double stranded nucleic acid. The intercalator-nucleic acid conjugate alternatively can be covalently coupled to a carrier protein. The nucleic acid portion of the immunogen can comprise the specific paired sequences found in the assay hybrid or can comprise any other desirable sequences since the specificity of the antibody will generally not be dependent upon the particular base sequences involved. Further information regarding antibodies to intercalation complexes is provided in commonly assigned U.S. Pat. No. 4,563,417.

As stated above, the antibody reagent can consist of whole antibodies, antibody fragments, polyfunctional antibody aggregates, or in general any substance comprising one or more specific binding sites from an antibody. When in the form of whole antibody, it can belong to any of the classes and subclasses of known immunoglobulins, e.g., IgG, IgM, and so forth. Any fragment of any such antibody which retains specific binding affinity for the hybridized probe can also be employed, for instance, the fragments of IgG conventionally known as Fab, F(ab'), and F(ab')2. In addition, aggregates, polymers, derivatives and conjugates of immunoglobulins or their fragments can be used where appropriate.

The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunoglobulins can also be obtained by somatic cell hybridization techniques, such resulting in what are commonly referred to as monoclonal antibodies, also involving the use of an appropriate immunogen.

In those instances where an antibody reagent selective for intercalation complexes is employed as one of the binding reagents, a variety of intercalator compounds can be involved. In general it can be said that the intercalator compound preferably is a low molecular weight, planar, usually aromatic but sometimes polycyclic, molecule capable of binding with double stranded nucleic acids, e.g., DNA·DNA, DNA·RNA, or RNA·RNA duplexes, usually by insertion between base pairs. The primary binding mechanism will usually be noncovalent, with covalent binding occurring as a second step where the intercalator has reactive or activatable chemical groups which will form covalent bonds with neighboring chemical groups on one or both of the intercalated duplex strands. The result of intercalation is the spreading of adjacent base pairs to about twice their normal separation distance, leading to an increase in molecular length of the duplex. Further, unwinding of the double helix of about 12 to 36 degrees must occur in order to accomodate the intercalator. General reviews and further information can be obtained from Lerman, J. Mol. Biol. 3:18(1961); Bloomfield et al, "Physical Chemistry of Nucleic Acids", Chapter 7, pp. 429–476, Harper and Rowe, NY(1974); Waring, Nature 219:1320 (1968); Hartmann et al, Angew. Chem., Engl. Ed. 7:693(1968); Lippard, Accts. Chem. Res. 11:211(1978); Wilson, Intercalation chemistry(1982), 445; and Berman et al, Ann. Rev. Biophys. Bioeng. 10:87(1981); as well as U.S. Pat. No. 4,563,417. Exemplary of intercalators are acridine dyes, e.g., acridine orange, the phenanthridines, e.g., ethidium, the phenazines, furocoumarins, phenothiazines, and quinolines.

The intercalation complexes are formed in the assay medium during hybridization by use of a probe which has been modified in its complementary, single stranded region to have the intercalator chemically linked thereto such that upon hybridization the intercalation complexes are formed. Essentially any convenient method can be used to accomplish such linkage. Usually the linkage is formed by effecting intercalation with a reactive, preferably photoreactive intercalator, followed by the linking reaction. A particularly useful method involves the azidointercalators. Upon exposure to long wavelength ultraviolet or visible light, the reactive nitrenes are readily generated. The nitrenes of arylazides prefer insertion reactions over their rearrangement products [see White et al, Methods in Enzymol. 46:644(1977)]. Representative azidointercalators are 3-azidoacridine, 9-azidoacridine, ethidium monoazides, ethidium diazide, ethidium dimer azide "Mitchell et al, JACS 104:4265(1982)], 4-azido-7-chloroquinoline, and 2-azidofluorene. Other useful photoreactable intercalators are the furocoumarins which form [2+2] cycloadducts with pyrimidine residues. Alkylating agents can also be used such as bis-chloroethylamines and epoxides or aziridines, e.g., aflatoxins, polycyclic hydrocarbon epoxides, mitomycin, and norphillin A. The intercalator-modified duplex is then denatured to yield the modified single stranded probe.

With reference to the drawings and the examples which follow, a few specific embodiments of the present assay scheme can be described.

The method illustrated in FIG. 1, involves an FAD-labeled polynucleotide probe which is either RNA or DNA when the sample sequence of interest is RNA or is RNA when the sample sequence is DNA. An antihybrid antibody is selected to be specific for RNA·RNA or RNA·DNA hybrids, as the case may be. Upon formation of hybrids between the sequence of interest and the FAD-labeled probe, binding sites for the anti-hybrid are created. Binding of anti-hybrid to the now FAD-labeled hybrid renders the FAD label incapable of recombining with apoglucose oxidase. In contrast, the unhybridized or free probe comprises FAD available for recombination to form active glucose oxidase which acts on glucose to release hydrogen peroxide to be detected by colorimetric or fluorescent means.

Figure 2:
Figure 2:
Figure 2:
Figure 2:
Figure 2:
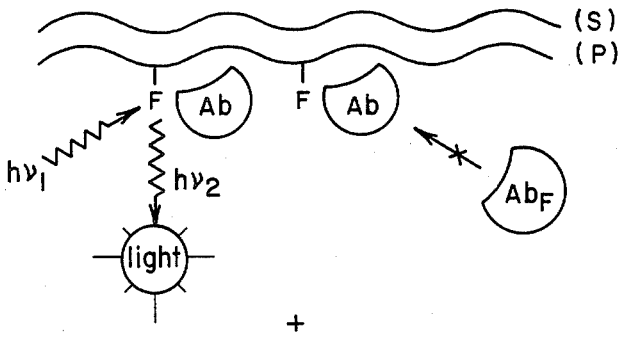
Figure 2:
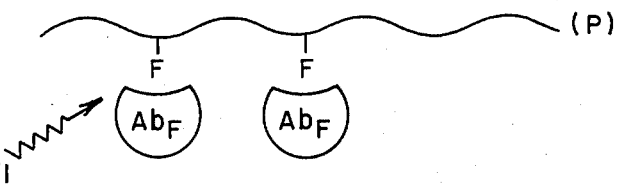

In the method shown in FIG. 2, the probe is in the FIG. 1 method except it is labeled with a fluorescer (F). Anti-hybrid and anti-fluorescer are added to the system. In the formed hybrid, the binding of anti-hybrid prevents the binding of anti-fluorescer to the label which retains its ability to fluoresce light ($hv_2$) upon irraditation ($hv_1$). However, the label in unhybridized probe is available for binding by anti-fluorescer resulting in quenching of fluorescence.

Figure 3:
Figure 3:
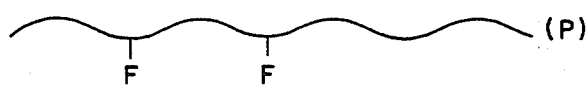
Figure 3:
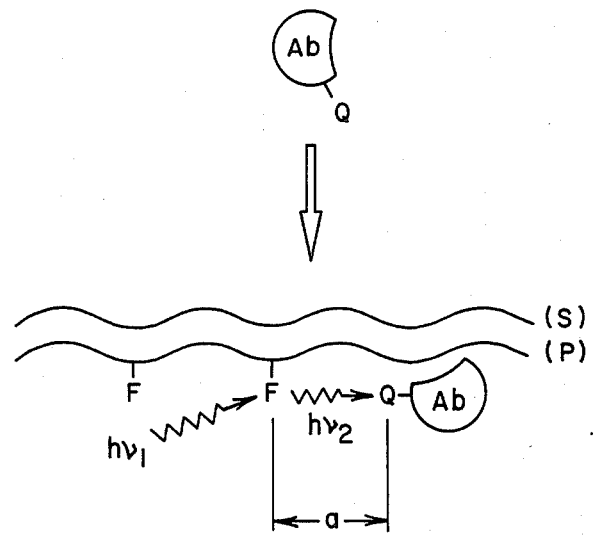
Figure 3:
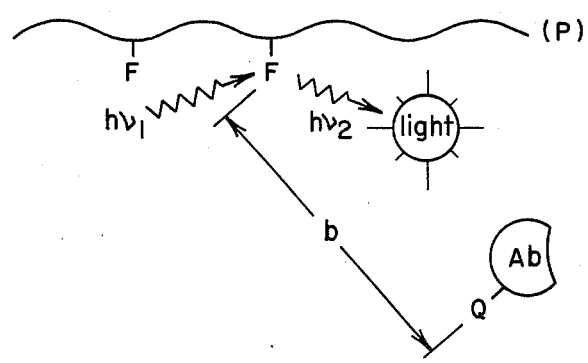

The method depicted in FIG. 3 employs a fluorescer(F)-labeled polynucleotide probe which is either RNA or DNA when the sample sequence of interest is RNA or is RNA when the sample sequence is DNA. An antibody selective for RNA·RNA or RNA·DNA hybrids, as the case may be, is labeled with a quenching moiety (Q). The fluorescer and quencher are brought into energy transfer distance a in the bound hybrid such that upon irradiation with light of a first wavelength ($hv_1$), the emitted energy ($hv_2$) is absorbed by the quencher and not detected. On the other hand, fluorescer-labeled probe in the bulk solution remains on average distance b from the quencher, which is not close enough for efficient energy transfer, and the fluorescence emission is observed. The amount of $hv_2$ light detected is inversely related to the amount of hybridization that occurs.

Reaction Mixture

The test sample to be assayed can be any medium of interest, and will usually be a liquid sample of medical, veterinary, environmental, nutritional, or industrial significance. Human and animal specimens and body fluids particularly can be assayed by the present method, including urine, blood (serum or plasma), milk, amniotic fluid cerebrospinal fluid, sputum, fecal matter, lung aspirates, throat swabs, genital swabs and exudates, rectal swabs, and nasopharnygal aspirates. Where the test sample obtained from the patient or other source to be tested contains principally double stranded nucleic acids, such as contained in cells, the sample will be treated to denature the nucleic acids, and if necessary first to release nucleic acids from cells. Denaturation of nucleic acids is preferably accomplished by heating in boiling water or alkali treatment (e.g., 0.1N sodium hydroxide), which is desired, can simultaneously be used to lyse cells. Also, release of nucleic acids can, for example, be obtained by mechanical disruption (freeze/thaw, abrasion, sonication), physical/chemical disruption (detergents such as Triton, Tween, sodium dodecylsulfate, alkali treatment, osmotic shock, or heat), or enzymatic lysis (lysozyme, proteinase K, pepsin). The resulting test medium will contain nucleic acids in single stranded form which can then be assayed according to the present hybridization method. In those situations where RNA·DNA hybrids are to be detected with labeled antibody reagents, mRNA and rRNA in the sample can be removed from participating in the binding reactions by conventional methods such as treatment with alkaline conditions, e.g., the same conditions used to denature the nucleic acids in the sample.

As is known in the art, various hybridization conditions can be employed in the assay. Typically, hybridization will proceed at slightly elevated temperatures, e.g., between about 35° and 75° C. and usually around 65° C., in a solution comprising buffer at pH between about 6 and 8 and with appropriate ionic strength (e.g., 5XSSC where 1XSSC=0.15M sodium chloride and 0.015M sodium citrate, pH 7.0). In cases where lower hybridization temperatures are desirable, hydrogen bonding reagents such as dimethyl sulfoxide and formamide can be included. The degree of complementarity between the sample and probe strands required for hybridization to occur depends on the stringency of the conditions. Factors which determine stringency are known in the art.

Normally, the temperature conditions selected for hybridization will be incompatible with the binding of the anti-hybrid reagent to formed hybrids and detection of the label response. Accordingly, the anti-hybrid binding step and label detection step will proceed after completion of the hybridization step. The reaction mixture will usually be brought to a temperature in the range of from about 3° C. to about 40° C. and the binding and detection steps then performed. Dilution of the hybridization mixture prior to addition of the antibody reagent is desirable when the salt and/or formamide concentrations are high enough to interfere significantly with the antibody binding reaction.

Reagent System

The present invention additionally provides a reagent system, i.e., reagent combination or means, comprising all of the essential elements required to conduct a desired assay method. The reagent system is presented in a commercially packaged form, as a composition or admixture where the compatability of the reagents will allow, in a test device configuration, or more usually as a test kit, i.e., a packaged combination of one or more containers, devices, or the like holding the necessary reagents, and usually including written instructions for the performance of assays. Reagent systems of the present invention include all configurations and compositions for performing the various hybridization formats described herein.

In all cases, the reagent system will comprise (1) a labeled nucleic acid probe as described herein, and (2) the antibody reagent. A test kit form of the system can additionally include ancillary chemicals such as the components of the hybridization solution and denaturation agents capable of converting double stranded nucleic acids in a test sample into single stranded form. Preferably, there is included a chemical lysing and denaturing agent, e.g., alkali, for treating the sample to release single stranded nucleic acid therefrom.

The present invention will now be illustrated, but is not intended to be limited, by the following examples.

EXAMPLE I

Detection of Ribosomal RNA From Bacteria Using An FAD-Labeled DNA Probe

A. Flavin $N^6$-(6-aminohexyl)adenine dinucleotide [(aminohexyl)FAD] is prepared by the method of Morris et al, Anal. Chem. (1981)53:658. Apoglucose oxidase is prepared as described by Morris et al (1983) Meth. in Enzymol. 92:413. Antibody to RNA·DNA hybrid is prepared as described by Stuart et al, (1981) Proc. Nat'l. Acad. Sci. 78:3751. A 565 base pair fragment of the 16s ribosomal RNA sequence from *E. coli* has been cloned between Hind III sites of a pBR322 vector [Brosius et al (1978) Proc. Nat'l. Acad. Sci. 75:4801]. 5(3-Amino)allyldeoxyuridine triphosphate is synthesized by the method of Langer et al, (1981) Proc. Nat'l Acad. Sci. 78:6633.

B. Preparation of Labeled DNA Probe. The pBR322 plasmid containing the 565 base pair fragment of 16s ribosomal RNA is propagated in *E. coli* strain HB101 Rec. A and the 16s RNA fragment is excised by digestion with Hind III restriction endonuclease. The fragment is nick translated with 5-(3-amino)allyldeoxyuridine triphosphate using $^3$H-dATP to monitor the incorporation as described by Langer et al, supra. This procedure provides a double stranded DNA with primary amino groups distributed along its length.

The complementary DNA strand is isolated by hybridization with 16s RNA from *E. coli* available from Boehringer Mannheim Biochemicals, Indianapolis, Ind. The nick translated probe is hybridized with excess 16s RNA as described by Casey and Davidson, (1977) Nucl. Acids Rec. 4:1539. The hybridization mixture is fractionated by equilibrium density gradient centrifugation at 23° C. for 48 hours at 33,000 rpm in an SW39 rotor (Beckman Instruments). The $Cs_2SO_4$ solution is adjusted initially to a density of 1.50 grams per cubic centimeter (g/cm$^3$) and at the end of the run the DNA is banded at a density of 1.45 g/cm$^3$, the RNA·DNA is at 1.52 and the excess RNA is at 1.6 g/cm$^3$. [Bassel, Hagaski and Spiegelman, 52:796(1964)].

The RNA·DNA is collected and the RNA strand is hydrolyzed in 0.1 molar (M) sodium hydroxide for six hours at room temperature. Then the hydrolysis mixture is adjusted to pH 7.0 with dilute acetic acid and the DNA is precipitated with cold 80% ethanol. The DNA is dissolved in 1M triethylammonium bicarbonate buffer, pH 9.3, and this solution is made 3 millimolar (mM) with dimethyladipimidate dihydrochloride and allowed to react for 5 minutes at room temperature. The excess bifunctional linking reagent is removed by gel filtration on Sephadex G-50, fine, (Pharmacia Fine Chemicals, Piscataway, N.J.) equilibrated with 20 mM sodium carbonate buffer, pH 9.3 at 5° C. The chromatography was completed in less than 15 minutes and effluent containing the DNA is immediately combined with an equal volume of 1 mM (aminohexyl) FAD which is in water. This reaction mixture is allowed to stand at room temperature for 2.5 hours and then the excess (aminohexyl)FAD is removed by gel filtration in a column of Sephadex G-25, medium, in 0.1M sodium phosphate buffer, pH 7.0. The reaction products separate into two yellow bands and the first to elute is collected and used for hybridization assays.

C. Hybridization Assay for detection of 16s Ribosomal RNA. Various size aliquots of an *E. coli* liquid culture are measured into a series of centrifuge tubes to give 10$^5$ to 10$^9$ cells per tube. The suspensions are centrifuged at 10,000×g for 10 minutes and the supernatants are discarded. The cells in each tube are suspended in 20 microliters (μl) of 10 milligrams per milliliter (mg/ml) egg white lysozyme (Sigma Chemical Co., St. Louis, Mo.) in 10 mM Tris-hydrochloride buffer, pH 8.0, 0.1M NaCl and 5 mM ethylendiaminetetraacetic acid. The lysates are extracted with phenol/chloroform by the procedure of Maniatis et al, Molecular Cloning, A Laboratory Manual, Cold Spring Harbor (1982). Polynucleotides in the extracts are precipitated with ethanol.

The precipitates are dissolved in 20 μl water and 80 μl of a solution composed of 60% formamide and 40% 0.16M sodium phosphate buffer, pH 6.5, 1.44M NaCl and 0.1% (w/v) sodium dodecylsulfate is added. Twenty microliters of the labeled DNA probe, 5 ng DNA, in 0.1M sodium phosphate buffer, pH 6.5, is added. The reaction tubes are sealed and incubated at 5° C. for 18 hours. Then the tubes are opened and 500 μl of antibody to RNA·DNA hybrid is added and allowed to react for 1 hour at room temperature.

The following reagents are used for the assay of glucose oxidase activity:

Composite reagent—92 mM sodium phosphate, pH 7.0, 0.1% bovine serum albumin, 2 mM 3,5-dichloro-2-hydroxybenzene sulfonate, 0.1M glucose, 20 mg peroxidase per ml. Apoglucose oxidase reagent—4 μM apoglucose oxidase binding sites, 25% glycerol, 4.0 mM 4-aminoantipyrine, and 0.01% (w/v) sodium azide.

After the hybridization reactions are incubated with the antibody, 1.9 ml of the composite reagent is added to each tube followed by 0.1 ml of apoglucose oxidase reagent. The mixtures are incubated at 25° C. for 30 minutes and at the end of this period the absorbances at 510 nm are recorded. As the quantity of bacteria increases, the absorbances will decrease due to increasing quantities of ribosomal RNA hybridized to the labeled probe.

EXAMPLE II

Hybridization Assay Monitored By Fluorescence Quenching

A. Antibody to fluorescein is raised with a fluorescein bovine serum albumin conjugate [Ullman, (1976) U.S. Pat. No. 3,998,943].

B. 6-Carboxyfluorescein is synthesized by the method of Ullman et al (1976) J. Biol. Chem. 251:4172. (The synthesis gives a mixture of isomers.) The N-hydroxysuccinimide ester is prepared as described by Khanna and Ullman (1980) Anal. Biochem. 108:156 for preparation of a corresponding ester of 4′,5′-dimethoxy-6-carbomethylfluorescein.

C. The nick translated probe containing 4-(3-amino)allyldeoxyuridine monophosphate residues described in Example 1, section B is dissolved from the ethanol precipitation step in 100 mM sodium phosphate buffer, pH 8.0 and made 2 mM with the N-hydroxysuccinimide ester of 6-carboxymethylfluorescein. This reaction mixture is allowed to stand overnight and then is fractionated by gel filtration on Sephadex G-25, medium, equilibrated with 0.1M sodium phosphate buffer pH 8.0. The first eluted peak of fluorescent material excitation, 490 nanometers (nm), emission 520 nm is the fluorescein labeled probe and is used for hybridization assays. D. The cell lysates described in Example I, Part C, are combined with 80 μl of 60% formamide and 40% 0.16 M sodium phosphate buffer, pH 8.0, 1.44 M NaCl and 0.1% sodium dodecylsulfate. Twenty microliters of fluorescein labeled probe (5 ng DNA) in 0.1 M sodium phosphate buffer, pH 8.0, is added to each extract tube. The tubes are stoppered tightly and incubated at 55° C. for 18 hours. Then 500 μl of antibody to RNA·DNA hybrid is added to each tube and allowed to stand for at least 1 hour at room temperature. The concentration of antibody is determined in preliminary experiments to provide a large excess over that required to bind all RNA·DNA hybrids expected.

Finally 400 μl of antibody to fluorescein is added and ten minutes later the fluorescence is recorded with 495 nm for excitation and 519 nm for emission. As the number of bacteria increases, the amount of ribosomal RNA will increase and quenching of fluorescence by antibody to fluorescein will decrease. Therefore, the fluorescence will increase as the number of bacteria increases.

EXAMPLE III

Hybridization Assay for Cytomegalovirus Using Fluorescence Energy Transfer

A. Preparation of a fluorescein labeled probe for cytomegalovirus

Cloned EcoRI restriction fragments of cytomegalovirus DNA are prepared as described by Tamashiro, et al (1982) Virology 42:547. The 1500 base pair fragment designated EcoRI e in the Tamashiro reference is used for preparation of the probe. The fragment is removed from the plasmid with EcoRI restriction enzyme and cloned into the corresponding site of the M13 mp8 vector (New England Biolabs, Beverly, MA). The virus is grown in E. coli K12JM101 and the single stranded virion DNA is isolated.

The viral DNA in 20 mM Tris-hydrochloride buffer, pH 8.0, containing 10 mM $MgCl_2$ is annealed to a molar excess of a 17 base primer GTAAAACGACGG-CCAGT (New England Biolabs) at 55° C. for 45 minutes [Bankier and Barrell, (1982) Techniques in Nucleic Acid Biochemistry, Elsevier, Ireland]. This primer is complementary to a region of the M13 mp8 DNA near the 3'-OH end of the EcoRI e insert. Then the reaction mixture is made 15 mM in dATP, dCTP, dGTP and 5(3-amino(allyl-dUTP. [Langer et al, supra] and the Klenow fragment of DNA polymerase I is added. The reaction is incubated at 25° C. for a period determined in preliminary experiments. For these experiments, samples are taken from the reaction mixture at various times and electrophoresed in denaturing alkaline agarose gel [Maniatis et al, supra]. The reaction time is optimized to give newly synthesized fragments that extend at least through the EcoRI e insert and some extension beyond the insert into the M13 mp8 sequence is acceptable for the present application.

Next, ethidium residues are coupled to the DNA probe as intercalation complexes. 8-azidoethidium is prepared by the method of Graves et al Biochim. Biophys. Acta 479:97 (1977). The DNA probe prepared above is extracted with phenol/chloroform and precipitated with ethanol. It is dissolved in 50 mM Tris-hydrochloride buffer, pH 8.0, 0.2 M NaCl and made 0.5 mM with 8-azidoethidium. The mixture is prepared in a glass reaction vessel and immersed in a glass water bath maintained at 20° to 30° C. Photolysis is conducted for 1 hour 10 to 20 cm from a 150 watt spotlight.

Noncovalently bound ethidium azide and photolysis by-produts are removed from the reaction mixture by 10 successive extractions with water saturated N-butanol. Residual butanol is removed by precipitation of the DNA with ethanol and the DNA is dissolved in the Tris buffer. Covalently bound ethidium residues is measured spectrophotometrically using the extinction coefficients $E_{490} \simeq 4 \times 10^3$ $M^{-1}$ $cm^{-1}$ for photolyzed ethidium azide, the relationship between $A_{260}$ and $A_{490}$ for photolyzed ethidium bound to DNA [$A_{260} = (A_{490} \times 3.4) - 0.011$] and $E_{260} \simeq 1.3 \times 10^4$ $M^{-1}$ $cm^{-1}$ for the DNA base pair concentration.

8-Azidoethidium binds covalently to the DNA mainly in the double stranded region where intercalation complexes can form. The objective is to incorporate one ethidium residues per 20 to 50 base pairs. The incorporation can be reduced by decreasing the photolysis time or decreasing the 8-azidoethidium concentration. Increased incorporation can be accomplished by repeating the photolysis with fresh 8-azidoethidium.

The primary amino groups of the 5(3-amino)allyl-dUMP residues in the DNA probe are reacted with the N-hydroxysuccinimide ester of 6-carboxyfluorescein. This reaction is carried out as outlined in Example II parts B and C above.

Finally the fluorescein labeled/ethidium modified probe is separated from the M13 mp8 template by electrophoresis in alkaline agarose gel [Maniatis et al, supra]. Since the probe is shorter than the vector DNA it migrates faster and can be recovered from the excised agarose slab by electroelution.

B. Preparation of monoclonal antibody to ethidium modified DNA

1. Preparation of covalent ethidium-DNA complexes

About 250 mg of salmon sperm DNA (Sigma Chemical Co., St. Louis, MO) is dissolved in 40 ml of 50 mM $NaCl_2$ and sheared by five passages through a 23 gauge needle. The sheared DNA is placed in a 250 ml flask and diluted with an additional 160 ml of buffer. One hundred forth-five microliters (145 $\mu$l) of $S_1$-nuclease, 200,000 units per ml (Pharmacia P-L Biochemicals, Piscataway, N.J.), is added and the mixture is incubated at 37° C. for 50 minutes.

Then the reaction mixture is extracted twice with phenol:chloroform, once with chloroform and the DNA is precipitated twice with ethanol [Maniatis et al (1982) "Molecular Cloning", Cold Spring Harbor Laboratory, Cold Spring Harbor, N.Y.]. The final precipitate is dissolved in 70 ml of 20 mM Tris hydrochloride buffer, pH 8.0.

This DNA is reacted with 8-azidoethidium under the following conditions. The reaction mixture is prepared with 33 ml of 2.7 mg DNA/ml, 13.5 ml of 4.95 mM 8-azidoethidium, 13.6 ml of 0.2 M Tris-hydrochloride buffer, pH 8.0 0.2 M NaCl, and 76 ml water. The mixture is placed in a 250 ml beaker with a water jacket maintained at 22° C. The mixture is stirred and illuminated for 60 minutes by a 150 watt spotlight at a distance of 10 cm. This photolysis is repeated with an identical reaction mixture.

The photolyzed reaction mixtures are combined and extracted 10-times with an equal volume each time of n-butanol saturated with 20 mM Tris-hydrochloride buffer, pH 8.0, 0.2 M NaCl. The extracted DNA solution is combined with 23 ml of 4.95 mM 8-azidoethidium and 77 ml of 20 mM Tris-hydrochloride buffer, pH 8.0, 0.2 M NaCl. This solution is photolyzed for 60 minutes as described above. The reaction products are extracted 10 times with buffer saturated butanol as described above and the DNA is precipitated with ethanol. The precipitate is dissolved in 10 mM Tris-hydrochloride buffer, pH 8.0, 1 mM EDTA and the absorbances at 260 and 590 nm are recorded.

2. Preparation of methylated thyroglobulin.

One hundred milligrams of bovine thyroglobulin (Sigma Chemical Co.) is combined with 10 ml of anhydrous methanol and 400 $\mu$l of 2.55 M HCl in methanol. This mixture is stirred on a rotary mixer at room temperature for 5 days. The precipitate is collected by centrifugation and washed twice with methanol and twice with ethanol. Then it is dried under vacuum overnight. About 82 mg of dry powder is obtained.

3. Preparation of ethidium-DNA/methylated thyroglobulin complex.

Methylated thyroglobulin (5.5 mg) is dissolved in 1.0 ml water and 1.1 ml of a 2.2 mg/ml ethidium-DNA solution is added. A precipitate forms immediately and the suspension is diluted to 30 ml with 0.15 M NaCl.

This suspension is emulsified with an equal volume of Freunds adjuvant.

4. Immunization of mice and preparation of monoclonal antibody.

BALB/c mice are immunized with 0.5 mL each of the emulsified immunogen. They are given booster injections biweekly and test bleeds are taken 5 to 7 days after the booster injections.

Antibody titers are assayed by standard enzyme label immunoadsorbent procedures. Immulon II (Dynateck, Alexandria, VA) microtiter wells are coated with single strand DNA, double strand DNA or the covalent ethidium-DNA intercalation complex by placing 50 $\mu L$ of a 5 $\mu g/mL$ solution in each well. The polynucleotides are in 0.15 M sodium citrate buffer, pH 6.8, 0.15 M NaCl. After the solutions stand in the wells at room temperature for 2 hours, the wells are washed with 0.02 M sodium phosphate buffer, pH 7.4, containing 5 mg bovine serum albumin/mL and 0.5% Tween 20 detergent (v/v). Appropriate dilutions of antiserums are added to the wells to allow binding of antibodies to the immobilized polynucleotide. The diluted antiserum is washed away and bound antibodies are detected with enzyme labeled antimouse IgG by well known procedures.

Mice with high titers to the covalent ethidium-DNA complex and very low titers to double and single stranded DNA are selected for further screening with immobilized noncovalent ethidium DNA complex. This involves coating wells with double stranded DNA and including 0.1 mM ethidium bromide in the antibody binding solution and all subsequent reagent and wash wolutions except the reagent for measurement of enzyme activity. Spleen cells from mice with high titers to the noncovalent ethidium-DNA complex are fused with myeloma cells to produce hybridomas [Poirer, et al, Proc. Nat'l. Acad. Sci., 79:6443 (1982); Galfre and Milstein, Meth. in Enzymol. 73:1 (1981)].

Cloned hybridomas are grown intraperitoneally in mice to raise large quantities of antibody. Albumin is removed from the ascites fluid by chromatography on Affigel-blue resin (Bio-Rad Laboratories, Richmond, CA) equilibrated with 10 mM Tris-hydrochloride buffer, pH 8.0, 0.15 M NaCl. The antibody passes directly through the column and is chromatographed on DEAE-Sepharose (Pharmacia Fine Chemicals, Piscataway, NJ) using a linear gradient of 10 mM Tris-hydrochloride buffer, pH 8.0, to this buffer containing 0.2 M NaCl. The major peak of eluted protein contains the antibody substantially free of other proteins.

C. Labeling of monoclonal antibody to ethidium-DNA with 4',5'-dimethoxy-6-carboxyfluorescein.

4',5'-Dimethoxy-6-carboxyfluorescein (synthesized as a mixture with the 4',5'-dimethoxy-5-carboxyfluorescein isomer) is converted to the N-hydroxysuccinimide ester as described by Khanna and Ullman, supra. This dye was conjugated to antibody to the ethidium-DNA intercalation complex by the method outlined in the reference.

D. Hybridization assay for cytomegalovirus.

Urine samples are centrifuged at 3000 rpm for 5 minutes in a Sorvall FLC-3 instrument to remove cellular and particulate matter. The supernatant is run in a polyallomer ultracentrifuge tube at 25,000 rpm in a Beckman Ti50 rotor for 75 minutes. The pellets are dissolved in 0.1 M NaOH and incubated at 37° C. for 30 minutes.

One hundred fifty microliters of 0.2 M sodium phosphate buffer, pH 6.,0, containing 1.8 M NaCl, 0.1% sodium dodecylsulfate (w/v) and 1 mM EDTA is added. Then 20 $\mu l$ of the fluorescein labeled/ethidium modified probe (50 ng) is added and the mixture is incubated at 65° C. for 10 hours. The reaction mixtures are cooled to room temperature and 650 $\mu L$ of 0.1 M Tris-hydrochloride buffer, pH 8.2, containing the labeled antibody to ethidium-DNA intercalation complex is added. The concentration of the labeled antibody in this reagent is optimized in preliminary experiments to give the maximum fluorescence quenching to background ratio. The reaction mixture is allowed to stand at room temperature for one hour.

Then the fluorescence of the reaction mixture is recorded using 495 nm light for excitation and 519 nm for emission. A urine that is not infected with cytomegalovirus is run in parallel and the fluorescence obtained with this control is higher than the fluorescence of the sample with virus. The fluorescence signal will increase as the virus level decreases.

The present invention has been particularly described and exemplified above. Obviously many other variations and modifications of the invention may be made without departing from the spirit and scope thereof.

What is claimed is:

1. A method for detecting a particular polynucleotide sequence in a test sample containing single stranded nucleic acids, comprising the steps of:
   (a) forming a hybrid between any of the particular polynucleotide sequence to be detected in the sample and a labeled nucleic acid probe comprising a label and at least one single stranded base sequence that is substantially complementary to the sequence to be detected, the hybrid having epitopes for an antibody reagent which does not bind substantially to single stranded nucleic acids,
   (b) contacting any hybrid that is formed with the antibody reagent, the label in the labeled probe providing a detectable response which is measurably different when the labeled probe is comprised in a hybrid that is bound by the antibody reagent compared to when not comprised in such a hybrid, and
   (c) measuring the detectable response as a function of the presence of the sequence to be detected in the sample.

2. The method of claim 1 wherein the antibody reagent is:
   (i) selective for binding DNA·RNA hybrids wherein one of the probe and the sequence to be detected is DNA and the other is RNA,
   (ii) selective for binding RNA·RNA hybrids wherein both the probe and the sequence to be detected are RNA, or
   (iii) selective for binding intercalation complexes wherein the duplexes formed in the assay comprise a nucleic acid intercalator bound thereto in the form of intercalation complexes.

3. The method of claim 1 wherein the label interacts with a reagent member of a label detection system to provide the detectable response and the detectable response is measurably different when the labeled probe is comprised in a hybrid that is bound by the antibody reagent compared to when not comprised in such a hybrid due to steric hindrance of access of such detection system member to the label.

4. The method of claim 3 wherein the label is a substrate, cofactor, or inhibitor of an enzyme which is the member of the label detection system with which the label interacts to provide the detectable response.

5. The method of claim 4 wherein the label is a substrate which is acted on by the enzyme to produce a colorimetric, fluorescent or luminescent signal.

6. The method of claim 4 wherein the label is a prosthetic group of an enzyme and wherein the apoenzyme of such enzyme is the member of the label detection system with which the label interacts to produce the catalytically active holoenzyme.

7. The method of claim 6 wherein the prosthetic group is FAD and the apoenzyme is apo(glucose oxidase).

8. The method of claim 3 wherein the label is a specifically bindable ligand for a binding substance which is the member of the label detection system with which the label interacts to provide the detectable response.

9. The method of claim 8 wherein the label is a hapten and its binding substance is a second antibody reagent.

10. The method of claim 9 wherein the label is fluorescent and wherein binding of the second antibody reagent thereto results in quenching of fluorescence.

11. The method of claim 9 wherein the detection system additionally comprises a conjugate of the hapten label, or a binding analog thereof, with an enzyme, the enzymatic activity of which conjugate is altered upon binding of the second antibody reagent thereto.

12. The method of claim 1 wherein the probe is labeled with one of a first label and a second label and the antibody reagent is labeled with the other, interaction between the first and second labels providing a detectable response which is measurably different when the labeled probe and labeled antibody reagent are both bound to the same hybrid compared to when they are not so bound.

13. The method of claim 12 wherein the first label participates in a first chemical reaction that produces a diffusible product which is a participant in a second chemical reaction with the second label to produce a product that provides the detectable response.

14. The method of claim 13 wherein the first and second labels are catalysts for the first and second chemical reactions, respectively.

15. The method of claim 14 wherein the antibody reagent is labeled with an enzyme.

16. The method of claim 15 wherein the probe is labeled with a nonenzyme catalyst.

17. The method of claim 12 wherein the first and second labels participate in an energy transfer interaction.

18. The method of claim 17 wherein the first label is a fluorescer or luminescer and the second label is a quencher.

19. The method of claim 1 wherein the probe is labeled with a fluorescer or luminescer, energy transfer interaction between the label and native groups on the antibody reagent providing a detectable response which is measurably different when the labeled probe is comprised in a hybrid that is bound by the antibody reagent compared to when not comprised in such a hybrid.

20. The method of claim 1 wherein the antibody reagent is selective for binding intercalation complexes and wherein the labeled probe also comprises a nucleic acid intercalator chemically linked to the probe in the single stranded complementary region of the probe whereby upon hybridization with the sequence to be detected said intercalation complexes are formed in the resulting hybrid.

21. The method of claim 1 wherein the label comprised in the labeled probe is chemically linked to the probe in its single stranded complementary region.

22. The method of claim 1 wherein the label comprised in the labeled probe is chemically linked to the probe in a region other than its complementary single stranded region.

23. The method of claim 1 wherein the test sample comprises a biological sample which has been subjected to conditions to release and denature nucleic acids present therein.

24. A reagent system for detecting a particular polynucleotide sequence in a test sample, comprising:
   (1) a labeled nucleic acid probe comprising a label and at least one single stranded base sequence that is substantially complementary to the sequence to be detected, and
   (2) an antibody reagent capable of binding to hybrids formed between any of the particular polynucleotide sequence to be detected in the sample and the labeled probe, but incapable of binding substantially to single stranded nucleic acids, the label providing a detectable response which is measurably different when the labeled probe is comprised in a hybrid that is bound by the antibody reagent compared to when not comprised in such a hybrid.

25. The reagent system of claim 24 wherein the antibody reagent is:
   (i) selective for binding DNA·RNA hybrids wherein one of the probe and the sequence to be detected is DNA and the other is RNA,
   (ii) selective for binding RNA·RNA hybrids wherein both the probe and the sequence to be detected are RNA, or
   (iii) selective for binding intercalation complexes wherein the duplexes formed in the assay comprise a nucleic acid intercalator bound thereto in the form of intercalation complexes.

26. The reagent system of claim 24 wherein the label interacts with a reagent member of the label detection system to provide the detectable response and the detectable response is measurably different when the labeled probe is comprised in a hybrid that is bound by the antibody reagent compared to when not comprised in such a hybrid due to steric hindrance of access of such detection system member to the label.

27. The reagent system of claim 26 wherein the label is a substrate, cofactor, or inhibitor of an enzyme which is the member of the label detection system with which the label interacts to provide the detectable response.

28. The reagent system of claim 27 wherein the label is a substrate which is acted on by the enzyme to produce a fluorescent or luminescent signal.

29. The reagent system of claim 27 wherein the label is a prosthetic group of an enzyme and wherein the apoenzyme of such enzyme is the member of the label detection system with which the label interacts to produce the catalytically active holoenzyme.

30. The reagent system of claim 29 wherein the prosthetic group is FAD and the apoenzyme is apo(glucose oxidase).

31. The reagent system of claim 26 wherein the label is a specifically bindable ligand for a binding substance which is the member of the label detection system with which the label interacts to provide the detectable response.

32. The reagent system of claim 31 wherein the label is a hapten and its binding substance is a second antibody reagent.

33. The reagent system of claim 32 wherein the label is fluorescent and wherein binding of the second antibody reagent thereto results in quenching of fluorescence.

34. The reagent system of claim 32 wherein the detection system additionally comprises a conjugate of the hapten label, or a binding analog thereof, with an enzyme, the enzymatic activity of which conjugate is altered upon binding of the second antibody reagent thereto.

35. The reagent system of claim 24 wherein the probe is labeled with one of a first label and a second label and the antibody reagent is labeled with the other, interaction between the first and second labels providing a detectable response which is measurably different when the labeled probe and labeled antibody reagent are both bound to the same hybrid compared to when they are not so bound.

36. The reagent system of claim 24 wherein the first label participates in a first chemical reaction that produces a diffusible product which is a participant in a second chemical reaction with the second label to produce a product that provides the detectable response.

37. The reagent system of claim 36 wherein the first and second labels are catalysts for the first and second chemical reactions, respectively.

38. The reagent system of claim 37 wherein the antibody reagent is labeled with an enzyme.

39. The reagent system of claim 38 wherein the probe is labeled with a nonenzyme catalyst.

40. The reagent system of claim 35 wherein the first and second labels participate in an energy transfer interaction.

41. The reagent system of claim 40 wherein the first label is a fluorescer or luminescer and the second label is a quencher.

42. The reagent system of claim 24 wherein the probe is labeled with a fluorescer or luminescer, energy transfer interaction between the label and native groups on the antibody reagent providing a detectable response which is measurably different when the labeled probe is comprised in a hybrid that is bound by the antibody reagent compared to when not comprised in such a hybrid.

43. The reagent system of claim 24 wherein the antibody reagent is selective for binding intercalation complexes and wherein the labeled probe also comprises a nucleic acid intercalator chemically linked to the probe in the single stranded complementary region of the probe whereby upon hybridization with the sequence to be detected said intercalation complexes are formed in the resulting hybrid.

44. The reagent system of claim 24 wherein the label comprised in the labeled probe is chemically linked to the probe in its single stranded complementary region.

45. The reagent system of claim 24 wherein the label comprised in the labeled probe is chemically linked to the probe in a region other than its complementary single stranded region.

46. The reagent system of claim 24 which additionally comprises a denaturation agent capable of converting double stranded nucleic acids in a test sample into single stranded form.

* * * * *